United States Patent [19]
Sugi et al.

[11] Patent Number: 5,082,654
[45] Date of Patent: Jan. 21, 1992

[54] CLATHRATE COMPOUND AND PROCESS FOR STABILIZING DIETHYLTOLUAMIDE

[75] Inventors: Hideo Sugi; Ryoichi Takahashi; Kenji Tahara, all of Tokyo, Japan

[73] Assignee: Kurita Water Industries Ltd., Tokyo, Japan

[21] Appl. No.: 423,378

[22] Filed: Oct. 19, 1989

[30] Foreign Application Priority Data

Oct. 28, 1988 [JP] Japan .................. 63-272716

[51] Int. Cl.$^5$ .................. A61K 31/165; A01N 27/00; C07C 233/65
[52] U.S. Cl. .................. 514/617; 514/919; 564/183
[58] Field of Search .................. 514/617, 919; 564/183; 424/412, 416, 79

[56] References Cited

U.S. PATENT DOCUMENTS 4,427,200  1/1984  Retnakaran et al. ............... 514/617
4,477,467  10/1984 Nishizawa et al. ................ 514/617

FOREIGN PATENT DOCUMENTS 326262  8/1989  European Pat. Off. ............ 514/919

Primary Examiner—Mukund J. Shah
Assistant Examiner—E. C. Ward
Attorney, Agent, or Firm—Kanesaka and Takeuchi

[57] ABSTRACT

A clathrate compound which comprises diethyltoluamide and a polymolecular host compound capable of taking up diethyltoluamide. The host compound is bisphenol compounds. Diethyltoluamide is stabilized by forming the clathrate compound.

4 Claims, 7 Drawing Sheets

CLATHRATE COMPOUND AND PROCESS FOR STABILIZING DIETHYLTOLUAMIDE

FIELD OF THE INVENTION AND RELATED ART STATEMENT

The present invention relates to a clathrate compound and a process for stabilizing diethyltoluamide. More particularly, it is concerned with a clathrate compound which eliminates the disadvantage of diethyltoluamide that it is poor in processing suitability, slow-acting property, and persistence because it is liquid and volatile although it is useful as an insect repellent, and also with a process for stabilizing diethyltoluamide.

Diethyltoluamide (N,N-diethyl-m-toluamide) is an insect repellent in the form of colorless or slightly yellowish liquid. It has been in generally used to protect human bodies from being bitten by bloodsucking insects such as mosquito and sand fly or to keep flies and cockroaches away.

It is used in the form of liquid spray or a mixture (such as cream). It is also infiltrated into paper, plastics, or plywood, or incorporated into paints and adhesives which are applied to a desired place.

Although diethyltoluamide is a very effective insect repellent, it has a disadvantage that it is poor in handling properties and processing suitability because it is a liquid as such. In addition, it is poor in persistence because of its comparatively high volatility.

OBJECTS AND SUMMARY OF THE INVENTION

It is an object of the present invention to provide a clathrate compound which improves the handling properties and processing suitability of diethyltoluamide and imparting the slow-volatilizing property to diethyltoluamide, thereby improving the persistence and stability of the insect repellent effect of diethyltoluamide, without any adverse effect, whereby to solve the above-mentioned problems.

It is another object of the present invention to provide a process for stabilizing diethyltoluamide which improves the handling properties and processing suitability of diethyltoluamide and imparting the slow-volatilizing property to diethyltoluamide, thereby improving the persistence and stability of the insect repellent effect of diethyltoluamide, without any adverse effect.

According to the present invention, the clathrate compound comprises diethyltoluamide and a polymolecular host compound capable of taking up diethyltoluamide.

According to the present invention, the process for stabilizing diethyltoluamide comprises reacting diethyltoluamide with a polymolecular host compound capable of taking up diethyltoluamide.

DETAILED DESCRIPTION OF PREFERRED EMBODIMENTS

Figure 1:
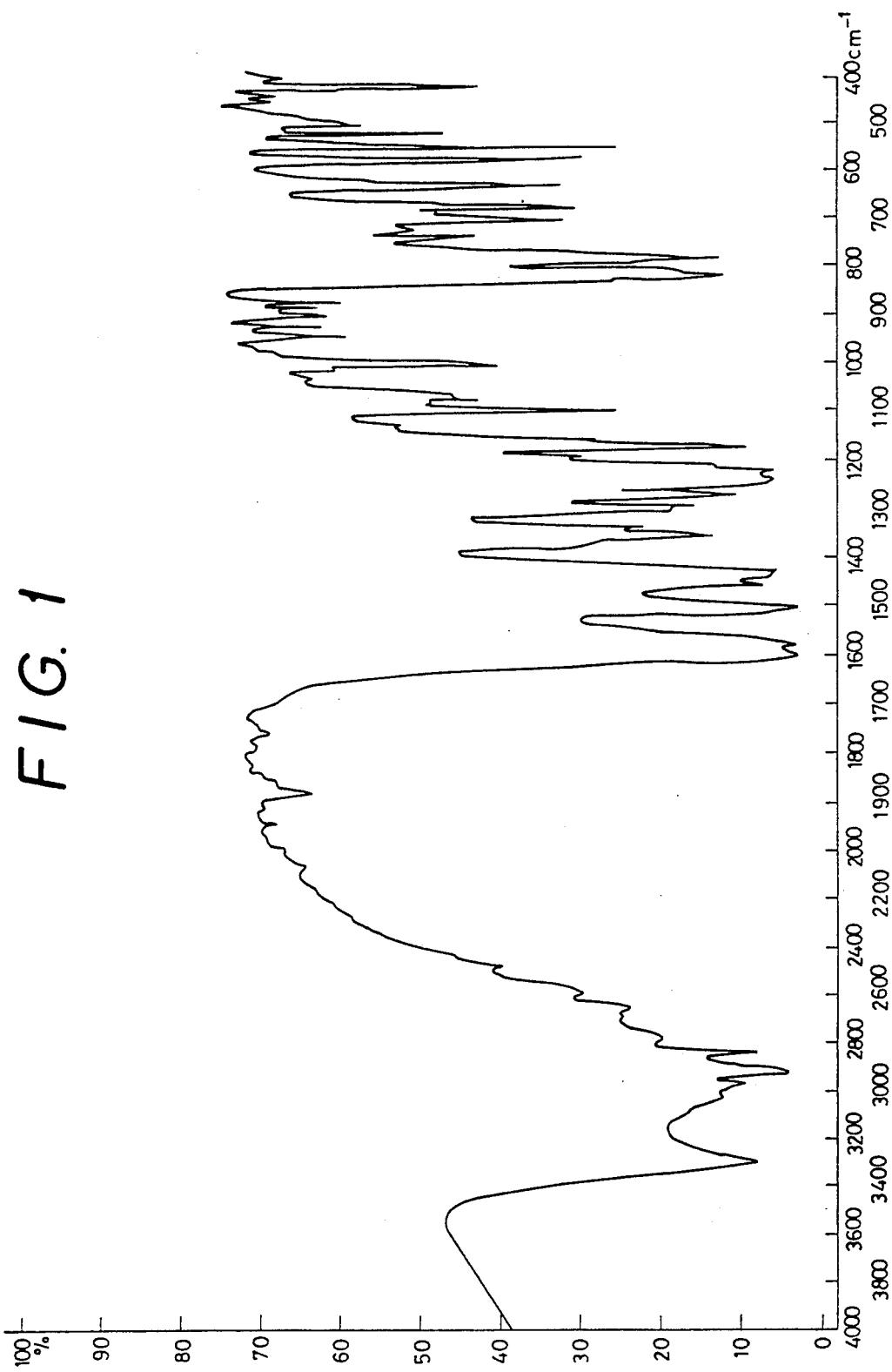
FIG. 1 is an IR spectrum of the clathrate compound obtained in Example 1.

The clathrate compound of the present invention is composed of diethyltoluamide as the guest compound and a polymolecular host compound capable of taking up the guest compound.

According to the present invention, the polymolecular host compound which takes up diethyltoluamide is one or more than one species selected from the compounds represented by the formulas I, II, and III below.

I. Bisphenol compounds represented by the formula [I] below.

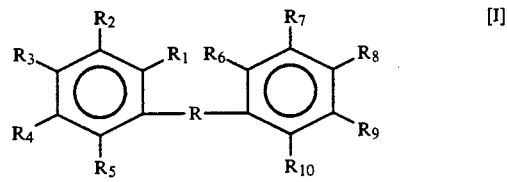

Where R denotes an alkylene group, an alkylidene group, sulfur atom, or sulfone; and $R_1$ to $R_{10}$ independently denote a hydrogen atom, hydroxyl group, halogen atom, or alkyl group, with at least one of $R_1$ to $R_5$ and at least one of $R_6$ to $R_{10}$ being a hydroxyl group.

II. Hydroquinone compounds represented by the formula [II] below.

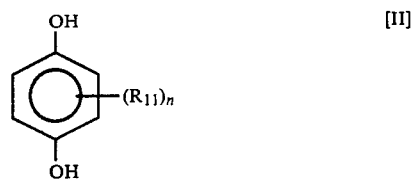

where $R_{11}$ denotes a branched alkyl group having 3–7 carbon atoms; and n is 1 or 2.

III. Bile acids represented by the formula [III] below.

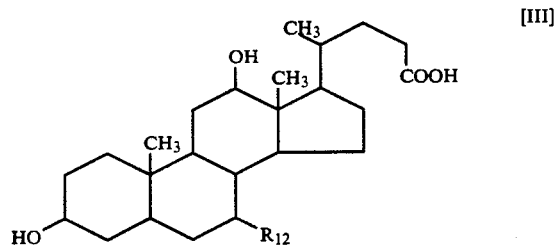

where $R_{12}$ is a hydrogen atom or hydroxyl group.

Examples of the bisphenol compounds [I] include 4,4'-cyclohexylidenebisphenol, bis(4-hydroxyphenyl)sulfone, 4,4'-butylidenebis(6-tert-butyl-3-methylphenol), 2,2'-methylenebis(4-methyl-6-tert-butylphenol), and 4,4'-thiobis(6-tert-butyl-3-methylphenol).

Examples of the hydroquinone compounds [II] include 2,5-di-tert-butylhydroquinone.

Examples of the bile acids [III] include deoxycholic acid.

The clathrate compound composed of a polymolecular host compound and diethyltoluamide can be easily prepared by mixing the two components in predetermined amounts, thereby directly reacting with each other, according to the process of the present invention for stabilizing diethyltoluamide.

According to the process of the present invention, the stabilization of diethyltoluamide is accomplished by reacting diethyltoluamide with a polymolecular host compound so that the latter takes up the former. The reaction may be accomplished by simply mixing the two reactants without using any solvent. Usually the reaction will be complete in 5 minutes at room temperature. The reaction ends when the reactants solidify. The clathrate compound thus formed is a crystalline powder. It is easily identified by its IR spectrum. If necessary, the reaction may be carried out in a solution such as chloroform, carbon tetrachloride, diethyl ether, and methylene chloride.

The ratio of diethyltoluamide to the polymolecular host compound should preferably be in the range of 10:90 to 90:10 (by weight). Therefore, the mixing ratio of the two reactants should be properly selected in this range.

The thus obtained clathrate compound composed of diethyltoluamide and a polymolecular host compound may be used in the form of crystalline powder. It may also be shaped into beads or pellets. It may also be dispersed into a solvent in the form of fine particles or incorporated into a paint, adhesive, or plastics resin.

The clathrate compound may be processed further to have persistance, such as slow-acting insect repellent paper, insect repelling plastic sheet, insect repellent plates, insect repellent paint, insect repellent adhesive, insect repellent spray, insect repellent cream, etc. for household use and industrial use.

The polymolecular host compound in the present invention takes up diethyltoluamide in an extremely stable manner and yet releases it at an adequately slow rate. Owing to this characteristic property, the clathrate compound of the present invention produces the following effects.

(1) It stably holds and protects diethyltoluamide.
(2) It prevents diethyltoluamide from volatilizing but releases it slowly.

Therefore, the clathrate compound of the present invention stably keeps the outstanding insect repellent effect of diethyltoluamide over a long period of time. In addition, since it has a form of powdery solid, it is superior in handling properties and processing suitability and can be applied to various forms.

According to the process of the present invention, diethyltoluamide is stabilized by forming the above-mentioned clathrate compound. Therefore, the process makes it possible to improve the stability and handling properties of diethyltoluamide without impairing its insect repellent effect.

The invention will be described in more detail with reference to the following examples and test examples, which are not intended to restrict the scope of the invention.

EXAMPLE 1

There was obtained a crystalline powder when 0.43 g of diethyltoluamide (DET for short hereinafter) was mixed with 1 g of 4,4'-cyclohexylidenebisphenol.

The crystalline powder was identified as a clathrate compound composed of DET and 4,4'-cyclohexylidenebisphenol by comparing its melting point and IR spectrum with those of 4,4'-cyclohexylidenebisphenol.

Figure 2:
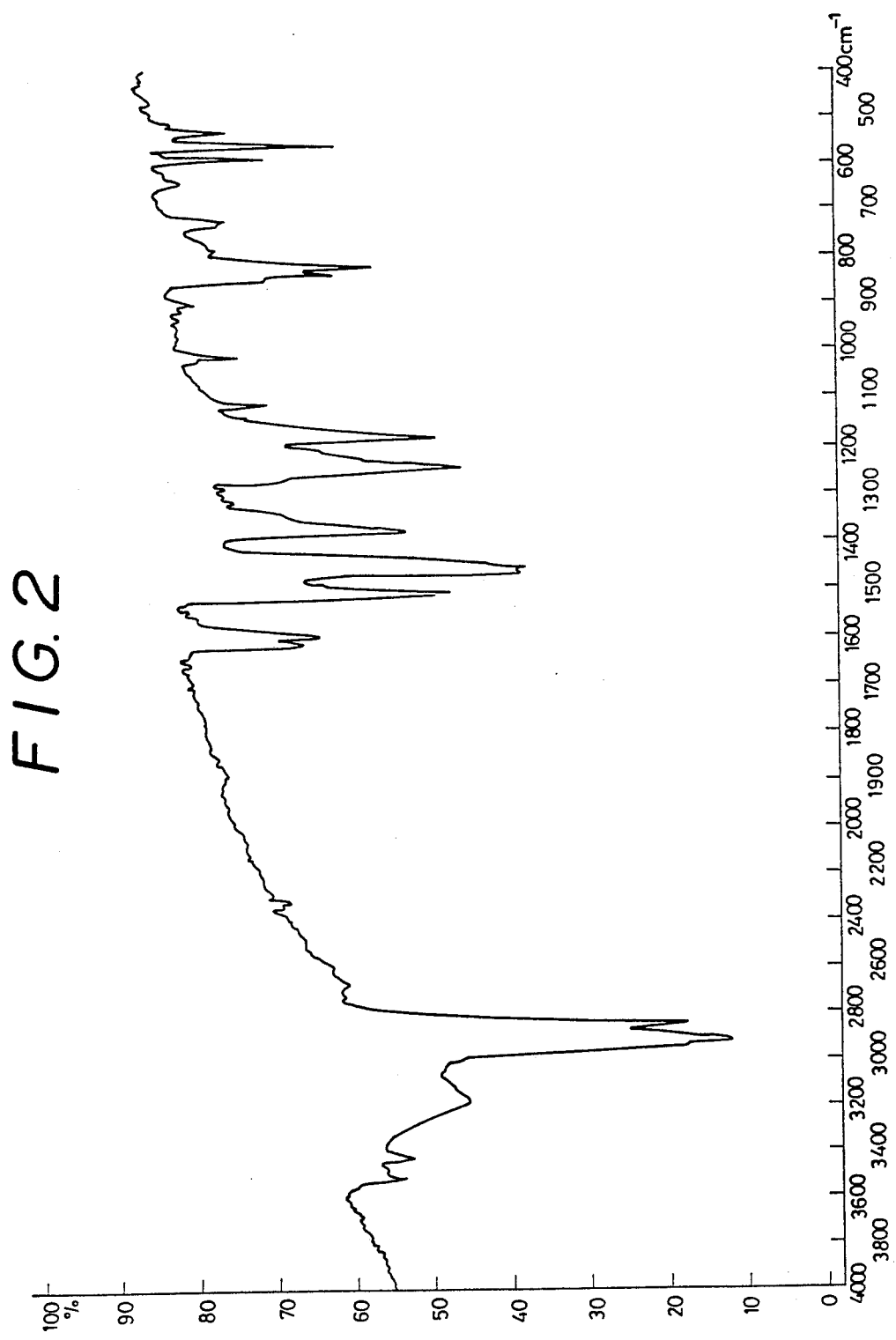
FIG. 2 is an IR spectrum of 4,4'-cyclohexylidenebisphenol.
Figure 3:
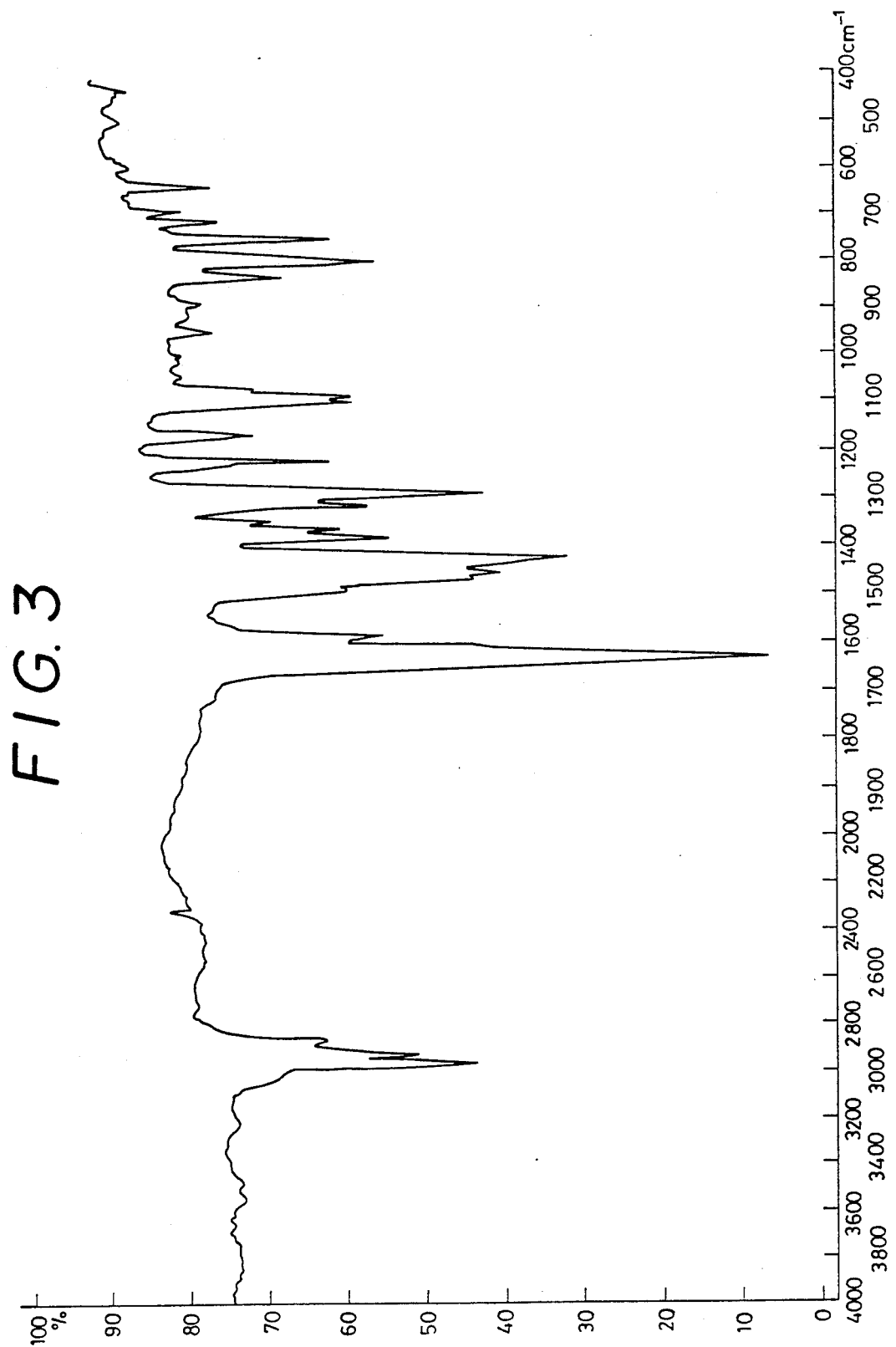
FIG. 3 is an IR spectrum of diethyltoluamide.

Table 1 shows the melting point of the clathrate compound and host compound. FIG. 1 shows the IR spectrum of the clathrate compound composed of DET and 4,4'-cyclohexylidenebisphenol. FIG. 2 shows the IR spectrum of 4,4'-cyclohexylidenebisphenol as the host compound. FIG. 3 shows the IR spectrum of DET as the guest compound.

EXAMPLE 2

There was obtained a crystalline powder when 0.85 g of DET was mixed with 1 g of 2,5-di-tert-butylhydroquinone. It was identified as a clathrate compound in the same manner as in Example 1.

Figure 4:
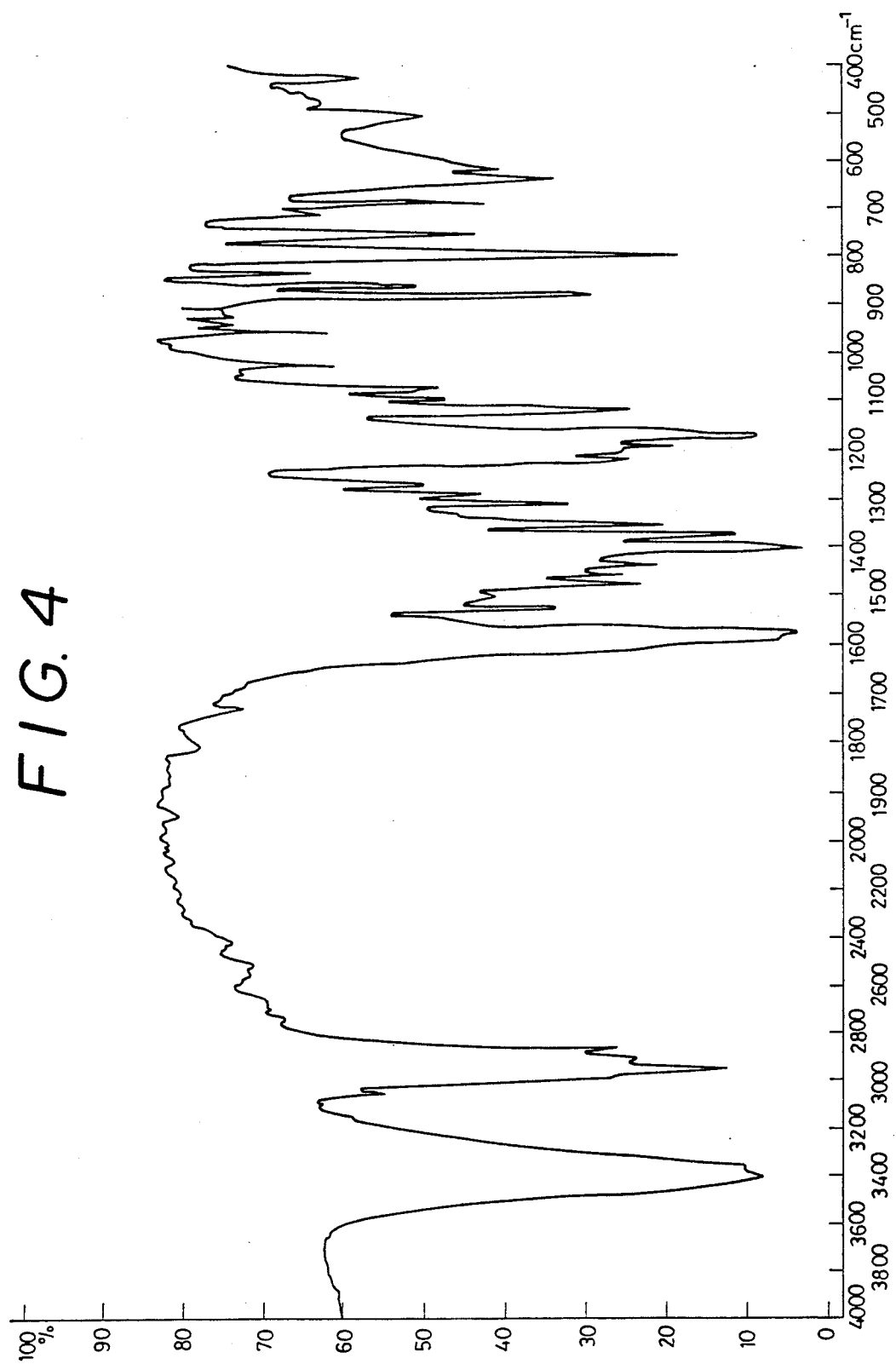
FIG. 4 is an IR spectrum of the clathrate compound obtained in Example 2.

Table 1 shows the melting point of the clathrate compound and 2,5-di-tert-butylhydroquinone. FIG. 4 shows the IR spectrum of the clathrate compound composed of DET and 2,5-di-tert-butylhydroquinone.

EXAMPLES 3 to 5

There was obtained a crystalline powder when a prescribed amount of DET was mixed with 1 g of the polymolecular host compound shown in Table 1. It was identified as a clathrate compound in the same manner as in Example 1.

Figure 5:
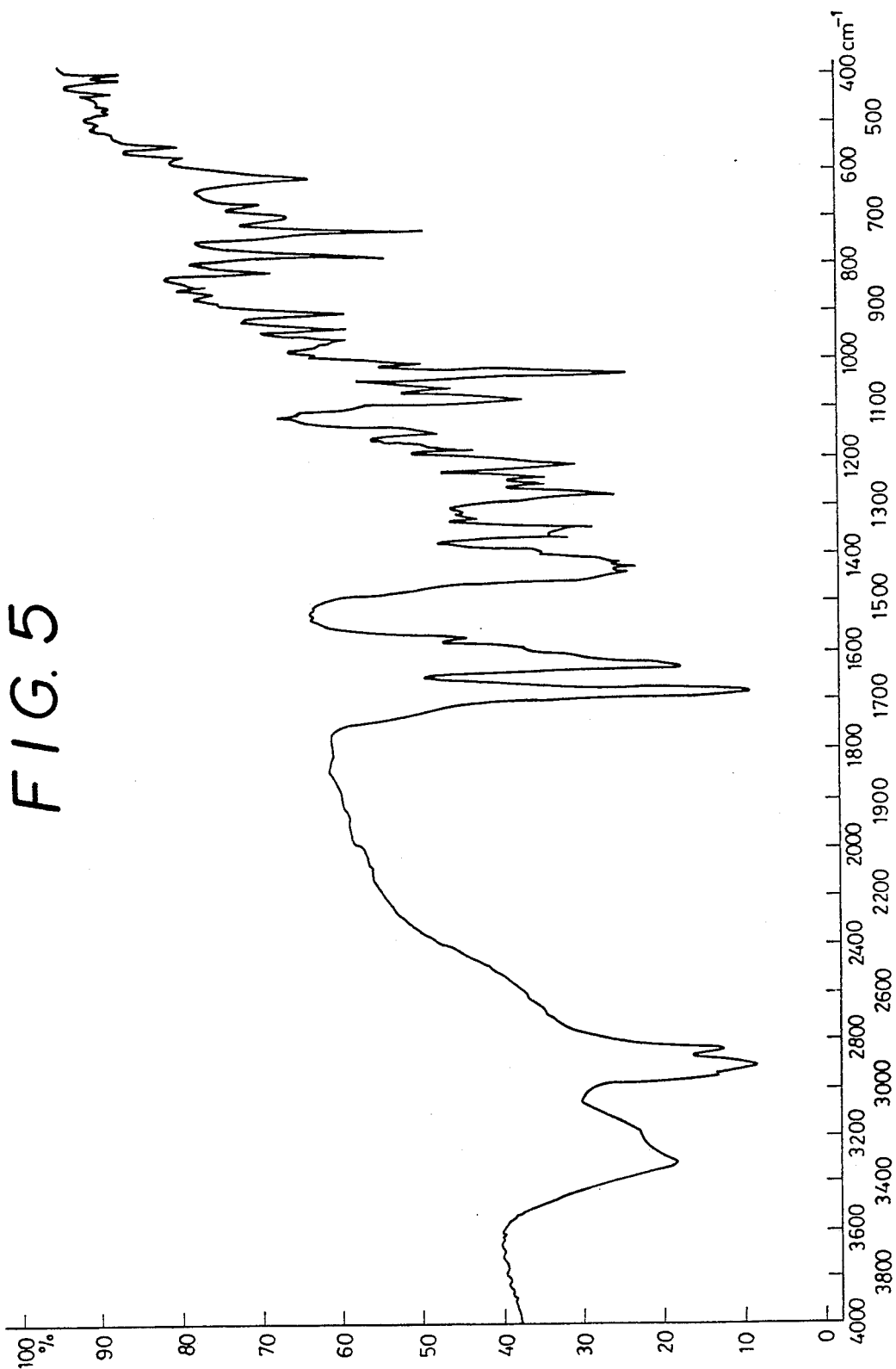
FIG. 5 is an IR spectrum of the clathrate compound obtained in Example 3.
Figure 6:
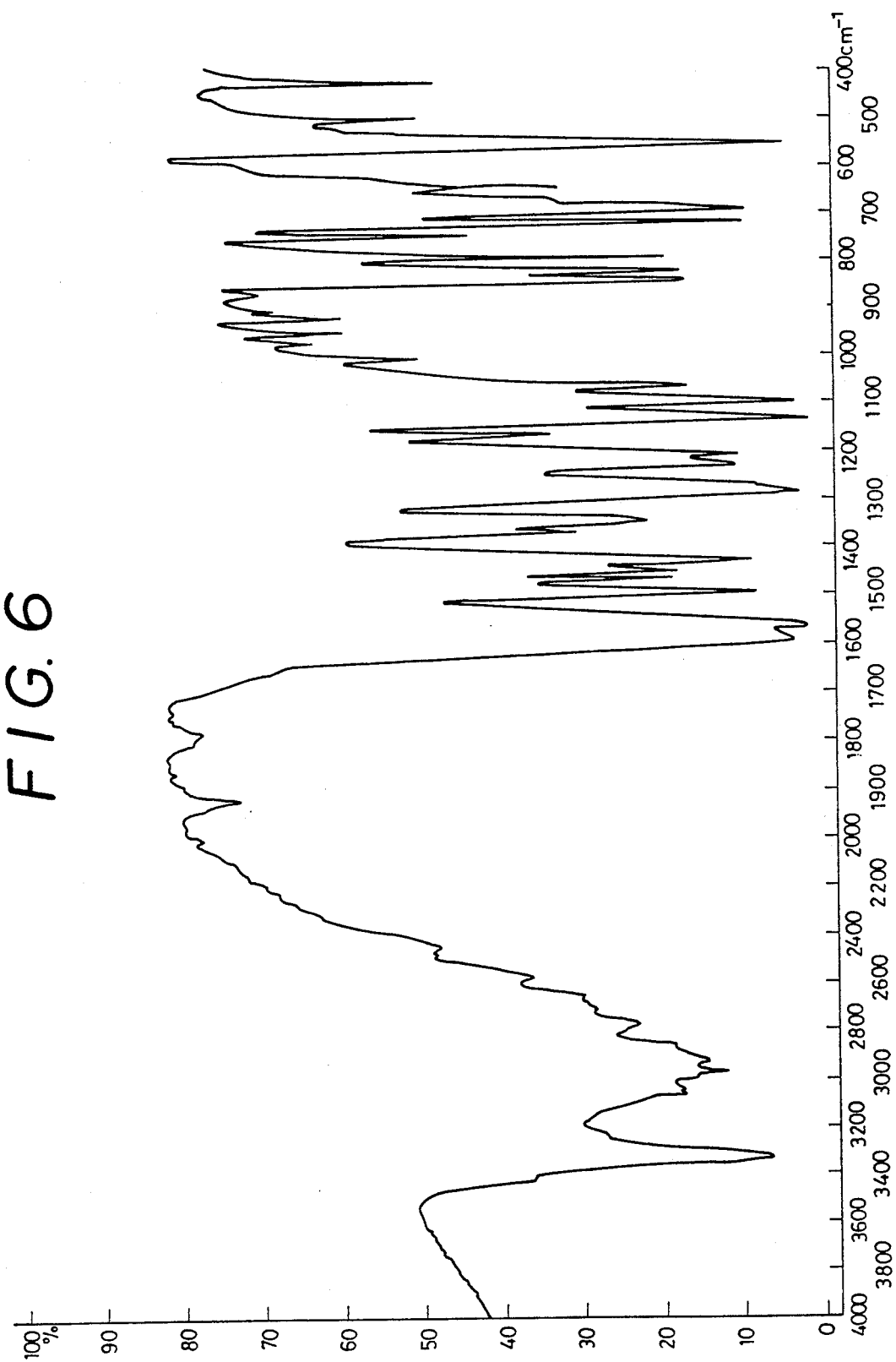
FIG. 6 is an IR spectrum of the clathrate compound obtained in Example 4.
Figure 7:
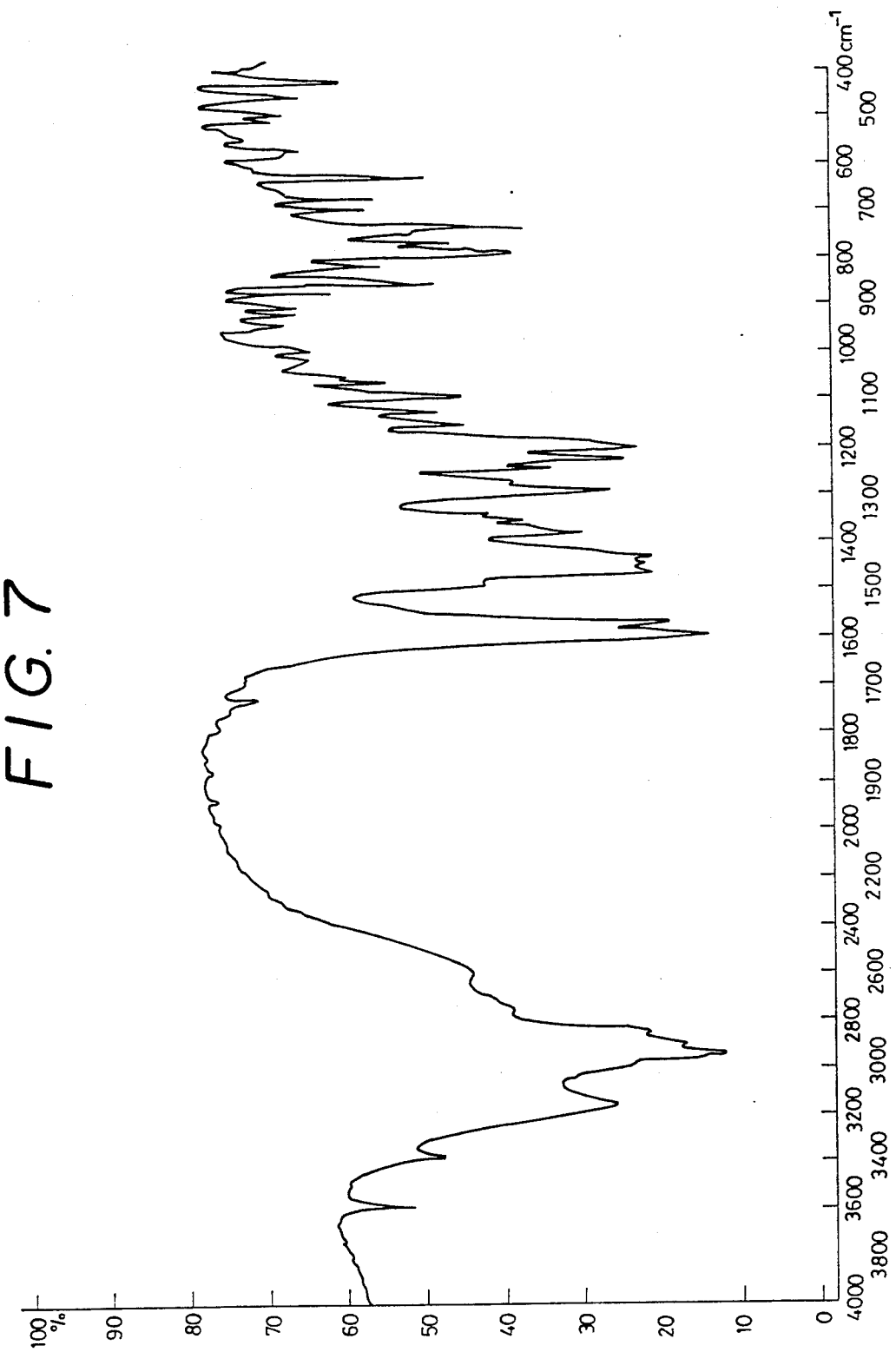
FIG. 7 is an IR spectrum of the clathrate compound obtained in Example 5.

Table 1 shows the DET content and melting point of the clathrate compound and the melting point of the polymolecular host compound. FIGS. 5 to 7 show the IR spectra of the clathrate compounds composed of DET and polymolecular host compound.

TABLE 1

| | | | Melting point (°C.) | |
| --- | --- | --- | --- | --- |
| Example | Polymolecular host compound | DET content (wt %) | Clathrate compound | Host compound |
| 1 | 4,4'-cyclohexylidene bisphenol | 30 | 77–130 | 180 |
| 2 | 2,5-di-tert-butylhydroquinone | 46 | 120–130 | 215 |
| 3 | Deoxycholic acid | 33 | 112–138 | 176–178 |
| 4 | Bis(4-hydroxyphenyl)sulfone | 43 | 137–141 | 253 |
| 5 | 2,2'-methylenebis(4-methyl-6-tert-butylphenol) | 36 | 96–100 | 127 |

TEST EXAMPLE 1

The clathrate compounds obtained in Examples 1 and 2 were tested for the slow-acting property by measuring their weight loss every day which occurred when they were allowed to stand in an atmosphere at 60° C. For the purpose of comparison, the weight loss of DET alone was also measured in the same manner. The results are shown in Table 2.

Each sample tested contained 0.3 g of DET, and the loss by volatilization is shown in terms of wt %.

Table 2 apparently shows that the clathrate compound of the present invention is by far superior in the slow-acting property.

TABLE 2

| Sample | Days elapsed | | | | | | | | | |
|---|---|---|---|---|---|---|---|---|---|---|
| | 1 | 2 | 3 | 4 | 5 | 6 | 7 | 8 | 9 | 10 |
| Control (DET alone) | 42.4 | 71.1 | 93.7 | 100 | — | — | — | — | — | — |
| Clathrate compound of DET and 4,4'-cyclohexylidene bisphenol | 25.6 | 38.8 | 50.5 | 61.5 | 73.4 | 85.1 | 93.7 | 100 | — | — |
| Clathrate compound of DET and 2,5-tert-butyl-hydroquinone | 6.1 | 10.0 | 14.1 | 19.3 | 23.6 | 28.4 | 33.2 | 36.5 | 40.9 | 43.0 |

What is claimed is:

1. A clathrate compound comprising diethyltoluamide and bisphenol compounds represented by the following formula, ratio of diethyltoluamide to bisphenol compounds being 10:90 to 90:10 by weight;

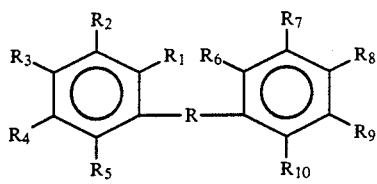

where R denotes an alkylene group having carbon number of 1–6, an alkylidene group having carbon number of 1–6, sulfur atom of sulfone; and $R_1$ to $R_{10}$ independently denote a hydrogen atom, hydroxyl group, halogen atom or alkyl group, with at least one of $R_1$ to $R_5$ and at least one of $R_6$ to $R_{10}$ being a hydroxyl group, said bisphenol compound being one or more species selected from the following compounds (a) to (e);
(a) 4,4'-cyclohexylidenebisphenol,
(b) bis(4-hydroxyphenyl) sulfone,
(c) 4,4'-butylidenebis(6-tert-butyl-3-methylphenol),
(d) 2,2'-methylenebis(4-methyl-6-tert-butylphenol),
(e) 4,4'-thiobis(6tert-butyl-3-methylphenol).

2. A process as claimed in claim 1, wherein the bisphenol compound is one or more than one species selected from the following compounds (a) to (e),
(a) 4,4'-cyclohexylidenebisphenol,
(b) bis(4-hydroxyphenyl)sulfone,
(c) 4,4'-butylidenebis(6-tert-butyl-3-methylphenol),
(d) 2,2'-methylenebis(4-methyl-6-tert-butylphenol),
(e) 4,4'-thiobis(6-tert-butyl-3-methylphenol).

3. A process for stabilizing diethyltoluamide comprising reacting diethyltoluamide and bisphenol compounds represented by the following formula to form a clathrate compound, ratio of diethyltoluamide to bisphenol compounds being 10:90 to 90:10 by weight;

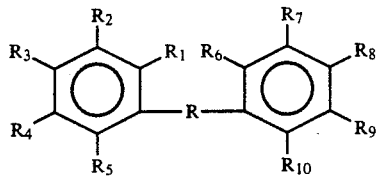

where R denotes an alkylene group having carbon number of 1-6, an alkylidene group having carbon number of 1-6, sulfur atom or sulfone; and $R_1$ to $R_{10}$ independently denote a hydrogen atom, hydroxyl group, halogen atom or alkyl group, with at least one of $R_1$ to $R_5$ and at leat one of $R_6$ to $R_{10}$ being a hydroxyl group.

4. A process for repelling insects consisting essentially of:

preparing a clathrate compound of diethyltoluamide and bisphenol compounds represented by the following formula, ratio of diethyltoluamide to bisphenol compounds being 10:90 to 90:10 by weight;

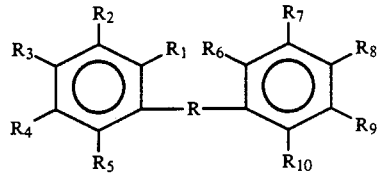

where R denotes an alkylene group having carbon number of 1-6, an alkylidene group having carbon number of 1-6, sulfur atom of sulfone; and $R_1$ to $R_{10}$ independently denote a hydrogen atom, hydroxyl group, halogen atom or alkyl group, with at least one of $R_1$ to $R_5$ and at least one of $R_6$ to $R_{10}$ being a hydroxyl group, said bisphenol compound being one or more species selected from the following compounds (a) to (e);
(a) 4,4'-cyclohexylidenebisphenol,
(b) bis(4-hydroxyphenyl)sulfone,
(c) 4,4'-butylidenebis(6-tert-butyl-3-methylphenol),
(d) 2,2'-methylenebis(4-methyl-6-tert-butylphenol),
(e) 4,4'-thiobis(6- tert-butyl-3-methylphenol),
incorporating the clathrate compound into a paint, adhesive or plastic resin, and
disposing the paint, adhesive or plastic resin with the clathrate compound to a desired place.

* * * * *